(12) United States Patent
Woerne (10) Patent No.: US 9,345,594 B2
(45) Date of Patent: May 24, 2016

(54) MODULAR STENT GRAFT

(71) Applicant: JOTEC GmbH, Hechingen (DE)

(72) Inventor: Christian Woerne, Ostfildern (DE)

(73) Assignee: JOTEC GmbH, Hechingen (DE)

( * ) Notice: Subject to any disclaimer, the term of this patent is extended or adjusted under 35 U.S.C. 154(b) by 0 days.

(21) Appl. No.: 14/445,810

(22) Filed: Jul. 29, 2014

(65) Prior Publication Data

US 2014/0336746 A1  Nov. 13, 2014

Related U.S. Application Data

(63) Continuation of application No. PCT/EP2013/051697, filed on Jan. 29, 2013.

(30) Foreign Application Priority Data

Jan. 31, 2012  (DE) .......................... 10 2012 100 754

(51) Int. Cl.
| | | |
|---|---|---|
| *A61F 2/07* | (2013.01) | |
| *A61F 2/852* | (2013.01) | |
| *A61F 2/89* | (2013.01) | |
| *A61F 2/06* | (2013.01) | |

(52) U.S. Cl.
CPC . *A61F 2/852* (2013.01); *A61F 2/07* (2013.01); *A61F 2/89* (2013.01); *A61F 2002/065* (2013.01); *A61F 2250/0037* (2013.01); *A61F 2250/0039* (2013.01); *A61F 2250/0062* (2013.01); *A61F 2250/0063* (2013.01)

(58) Field of Classification Search
CPC ......................................................... A61F 2/07
USPC ................................................ 623/1.13–1.36
See application file for complete search history.

(56) References Cited

U.S. PATENT DOCUMENTS

| | | |
|---|---|---|
| 5,824,037 A | 10/1998 | Fogarty et al. |
| 7,985,250 B2 | 7/2011 | Kaufmann et al. |

(Continued)

FOREIGN PATENT DOCUMENTS

| | | |
|---|---|---|
| DE | 10346200 | 5/2005 |
| DE | 102006004123 | 8/2007 |

(Continued)

OTHER PUBLICATIONS

Mailed Aug. 14, 2014—English Translation of the International Preliminary Report on Patentability (Chapter I).

*Primary Examiner* — Suzette J Gherbi
(74) *Attorney, Agent, or Firm* — Casimir Jones, S.C.

(57) ABSTRACT

The present invention relates to a modular stent graft which is designed for introduction into a blood vessel in a patient and which has a stent connected by means of a graft material; the stent graft has a first stent graft module having a body, a proximal end and a distal end, as well as at least three tubular arms extending longitudinally in the distal direction from the distal end of the first stent graft module, said arms being integrally connected to the body of the first stent graft module; in addition, a second stent graft module is provided which has a second body, a proximal end and a distal end, as well as at least three tubular arms extending longitudinally in the proximal direction from the proximal end of the second stent graft module, said arms being integrally formed with the body of the second stent graft module; in the assembled state a modular stent graft is formed, the modules of which are situated in the same blood vessel.

10 Claims, 4 Drawing Sheets

(56) References Cited

U.S. PATENT DOCUMENTS

| | | |
|---|---|---|
| 8,100,958 B2 | 1/2012 | Fischer |
| 8,668,729 B2 | 3/2014 | Kaufmann et al. |
| 2003/0120333 A1 | 6/2003 | Ouriel |
| 2004/0082990 A1* | 4/2004 | Hartley ........................ 623/1.13 |
| 2005/0010277 A1* | 1/2005 | Chuter ........................ 623/1.13 |
| 2006/0224228 A1* | 10/2006 | Dehdashtian et al. ....... 623/1.13 |
| 2006/0247757 A1 | 11/2006 | Kaufmann |
| 2009/0177265 A1* | 7/2009 | Dierking et al. ............ 623/1.13 |
| 2010/0137969 A1* | 6/2010 | Rakos et al. ................. 623/1.13 |
| 2010/0249899 A1* | 9/2010 | Chuter et al. ................ 623/1.13 |

FOREIGN PATENT DOCUMENTS

| | | |
|---|---|---|
| DE | 102007010305 | 8/2008 |
| DE | 10337739 | 11/2009 |
| WO | 00/76423 | 12/2000 |
| WO | 2006/028925 | 3/2006 |

* cited by examiner

MODULAR STENT GRAFT

CROSS-REFERENCES TO RELATED APPLICATIONS

This application is a continuation of international patent application PCT/EP2013/051697, filed on Jan. 29, 2013 designating the U.S., which international patent application has been published in German language and claims priority from German patent application DE 10 2012 100 754.3, filed on Jan. 31, 2012. The entire contents of these priority applications are incorporated herein by reference.

BACKGROUND OF THE INVENTION

The present invention relates to a modular stent graft composed of two stent graft modules for insertion into a blood vessel of a patient.

Stent grafts are generally understood as endoluminal prostheses or intra-vascular implants that are used in weakened, damaged, torn or aneurysmal vessels. For this purpose, a stent graft is released at the diseased or damaged site in the vessel and restores the functionality of the original vessel or supports the still existing integrity of the vessel. The stent graft, which is radially expandable, is for this purpose inserted into the vessel concerned and is radially enlarged or expanded.

Stent grafts are generally composed of a tubular, i.e. hollow cylindrical main body made of a biocompatible graft material, to which one or more stents or stent rings are attached. The stents presently used in the stent grafts are usually self-expanding and comprise what is called a shape-memory material, for example Nitinol, by means of which the whole stent graft is able to change from its non-compressed state to a compressed state and then, i.e. after release, can expand again to the non-compressed state. For insertion into the blood vessel to be treated, the stent graft is thus compressed and, in the compressed state, is inserted into the vessel until it comes to lie at the desired location. It is released there, i.e. it is allowed to expand to the non-compressed state. The walls of the stent graft then position themselves on the vessel wall and replace and/or support the latter. In this way, the defect is closed, and the blood carried in the vessel can flow through the tubular main body of the stent graft.

Stent grafts or vascular implants can generally be composed of a single stent graft body or, alternatively, of a plurality of separate but connectable stent graft bodies or stent graft modules. A modular stent graft has the advantage that it can be put together in a manner specific to the vessel/vessel area to be treated with the stent graft and to the different diameters or lengths of said vessel/vessel area. The individual separate modules of the stent graft are then generally inserted and assembled in situ, i.e. at the site to be treated in the vessel, so as to form a continuous stent graft. For this purpose, use is generally made of the fact that the ends of the individual stent graft modules overlap, and that one end of one stent graft module can be inserted with an overlap into one end of another stent graft module. As a result of the self-expanding force acting outward and in the direction of the vessel wall, the modules remain connected to one another in the overlapping areas by means of frictional forces.

Given the particular nature of the vessels to be treated in each case, prostheses are in many cases made available that are specifically tailored to the patient or to the vessels of the patient, in particular to the specific vessel to be treated, in order to meet the requirements concerning the necessary or desired length and diameter. This special and specific production is complex, expensive, labor-intensive and cost-intensive, since only one specific prosthesis can be produced in each case.

Therefore, there is still in principle a great need for prostheses that permit flexible use in order to meet the various requirements, particularly in terms of length and diameter, of the vessels of different patients. An object of the present invention is therefore to make available an alternative prosthesis system by which a tailor-made system, in particular a tailor-made system with respect to vessel length and diameter, is rendered superfluous.

SUMMARY OF THE INVENTION

According to the invention, this and other objects is achieved by the fact that a modular stent graft is made available which is designed for introduction into a blood vessel of a patient at a site where there is no bifurcation of blood vessels, and which has stents connected by means of a graft material, wherein the stent graft has the following: a first stent graft module with a body, a proximal end and a distal end, and with at least two to four tubular arms which extend longitudinally in the distal direction from the distal end of the first stent graft module and which are integrally connected to the body of the first stent graft module; a second stent graft module with a second body, a proximal end and a distal end, and with at least three tubular arms which extend longitudinally in the proximal direction from the proximal end of the second stent graft module and which are integrally formed with the body of the second stent graft module; arms of the first stent graft module and of the second stent graft module here in each case have diameters such that the first and second stent graft modules are connectable to each other by interlocking (or guiding or moving) one into the other and by partially overlapping the respective one arm of the distal end of the first stent graft module with the arm of the proximal end of the second stent graft module in order to form an assembled modular stent graft within the same blood vessel.

Here, as is generally the case in the prior art, a "stent graft module" is understood as an individual stent graft element of a stent graft or stent graft system which, in the non-implanted state, i.e. when not inserted into a blood vessel, comprises the individual, separate and non-interconnected stent graft modules and, after introduction of the individual stent graft elements into a vessel, forms within the latter an assembled stent graft/stent graft system composed of the stent graft elements. The stent graft elements or modules are connected to each other by an overlapping arrangement of the ends of the respective stent graft modules and remain as it were indirectly connected or anchored to each other by frictional adherence and by the radial expansion force of the stent elements of the individual stent graft modules.

Moreover, a "stent graft" or "stent graft module" is understood here as a vascular implant or vascular implant module which comprises a tubular or hollow cylindrical main body, with a biocompatible graft material to which one or more self-expanding stents or stent rings are attached. By virtue of the radially self-expanding stent rings or stent, the stent graft or the stent graft module is able to change from its originally non-compressed state to a compressed state for insertion into a vessel of a patient and then, i.e. after release, can expand again to the non-compressed state. For insertion into the blood vessel to be treated, the stent graft or stent graft module is thus compressed and, in the compressed state, is inserted into the vessel until it comes to lie at the desired location to be treated. It is released there, i.e. it is allowed to expand to the non-compressed state. The walls of the stent graft/stent graft module then position themselves on the vessel wall and replace and/or support the latter. In this way, the defect is closed, and the blood carried in the vessel can flow through the tubular main body of the stent graft.

Here, and throughout the description, the modular stent graft according to the invention is also designated synonymously as "modular stent graft system" or "modular stent graft assembly".

At present, modular stent grafts are customarily used at sites in blood vessels where side vessels branch off. The prostheses used here generally have side branches, which come to lie in the branching-off vessels. These modular vascular prostheses are used in order to arrange a sealing implant even at vessel ramifications and at the same time to prevent blockage of a branching-off vessel.

For example, WO 2000/076423 discloses a modular stent graft system or assembly composed of two tubular prostheses which are inserted and joined together at the area where the abdominal aorta branches into the iliac arteries.

WO 2006/028925 also describes a modular prosthesis system having a first module with a side branch and a second module with a notch; this system is used in the area of the aortic arch, where various vessels branch off.

US 2003/0120333 A1 discloses a prosthesis system with a plurality of modules, with a main module having a body, and with tubular arms extending in the distal direction. Legs can be attached separately to these arms in order to form stent graft branches that extend into branching-off vessels.

Moreover, U.S. Pat. No. 5,824,037 discloses a modular prosthesis system in which two or more tubular prostheses can be plugged into each other via ends that widen in a wedge shape.

The aforementioned documents therefore only describe the use of modular stent grafts at bifurcations, i.e. where blood vessels branch off. However, it was not known or disclosed to use modular stent grafts within the same vessel. Here, use of a modular stent graft within "the same vessel" is understood as meaning that the modular stent graft is not assembled and used at a branching-off of blood vessels, but instead at an unbranched site of the blood vessel, such that the two stent graft modules come to lie within the same vessel, i.e. not with one stent graft module in the main vessel and the other stent graft module in a vessel branching off from the main vessel.

According to the invention, this has the effect that the stent graft can be more easily inserted, since it is assembled in two steps, which permits more flexible release and simpler positioning. With the stent graft according to the invention, it is possible to easily achieve correct positioning without having to consider the specific length, dimension and design of the parts in respect of the vessel anatomy. Thus, for example, the specifically desired and required position can be obtained by rotating one or the other module in the vessel. In this way, the modular stent graft can be used flexibly, which not only ensures an individual use in each case but also permits a broader application to different vessels and patients.

In the case of stent grafts or endoluminal prostheses, the respective ends are generally designated, as here, by the terms "distal" and "proximal", where the term "distal" designates that part or end lying farther downstream in relation to the blood flow. By contrast, the term "proximal" designates, again in relation to the blood flow, a part or end lying farther upstream in relation to the blood flow. To put it another way, the term "distal" means in the direction of the blood flow, and the term "proximal" means counter to the direction of the blood flow. In catheters, by contrast, or insertion systems, the term "distal" designates the end of the catheter or insertion system that is introduced into the patient, or the end farthest away from the user, and the term "proximal" designates the end directed toward and closer to the user.

Both stent graft modules have stents or stent rings which, on the side facing the vessel wall, are connected to each other by a biocompatible graft material or prosthesis material. The stents constitute meandering rings made of a self-expanding material with a shape memory, preferably Nitinol, which have arches or supports alternately pointing in the proximal and distal directions. The arms of the stent graft modules are also constructed in this way. Such stents and the graft material/prosthesis material are described in more detail in DE 103 37 739, for example, the entire content of which is hereby specifically referred to.

The graft materials used in the present invention have a biocompatible material and are preferably chosen from polyesters, for example polyethylene terephthalates, polylactide, polyglycolide and copolymers thereof; also from polytetrafluoroethylene (PTFE), expanded PTFE (ePTFE) and polyvinylidene fluoride; polysiloxanes; polyurethanes, etc. In addition, materials can also be used which are not inherently biocompatible but which have been suitably treated. The graft material is preferably a woven material which has one or more of the aforementioned materials or consists of these.

According to the invention, the first stent graft module has at least two to four arms, in particular three arms, which extend longitudinally in the distal direction from the distal end of the module, i.e. in the direction of the blood flow. For example, various devices needed for the insertion, handling or use of the stent graft can be inserted into and through these arms, for example guide wires, catheters, stents, stent grafts, etc. A connection to branching-off vessel sections, for example to the celiac trunk and the superior mesenteric artery, is established via the arms.

The second stent graft module also has arms which, from its proximal end, extend in the proximal direction and thus point to the arms of the first stent graft module extending in the distal direction. The arms of the second stent graft module are provided to establish a connection to branching-off vessel sections such as the renal arteries, for example.

According to the invention, the diameter of an arm of the first stent graft module is adapted to the diameter of an arm of the second stent graft module in such a way that they can be guided into each other or plugged into each other, such that the ends of the arms at least partially overlap in situ. In this way, a part of the end of one stent graft module is relatively anchored in the other stent graft module. This telescopic fastening is generally achieved by frictional forces in the overlap region, and also by the radial force that the inside stent graft module exerts on the outside stent graft module.

Depending on which stent graft module is inserted and positioned first, either the distal end of the arm of the first stent graft module is situated in the proximal end of the second stent graft module, or, conversely, the proximal end of the arm of the second stent graft module is situated in the distal end of the arm of the first stent graft module. If the first stent graft module that comes to lie proximally is inserted and positioned first, the proximal arm of the second stent graft module is inserted into the distal end of the arm of the first stent graft module. If the second stent graft module is positioned first, the distal end of the arm of the first stent graft module is inserted into the proximal end of the arm of the second stent graft module and is anchored there.

This permits convenient, simple and flexible introduction of the modular stent graft in accordance with the vascular conditions found in each case.

Accordingly, in an embodiment of the modular stent graft according to the invention, the first stent graft module and the second stent graft module are connectable by interlocking an arm of the second stent graft module into an arm of the first stent graft module and by having them partially overlap, whereas, according to another preferred alternative, the first stent graft module and the second stent graft module are connectable by interlocking (or guiding or moving) an arm of the first stent graft module into an arm of the second stent graft module and by having them partially overlap.

According to yet another embodiment, the arms of the first stent graft module and/or of the second stent graft module have different lengths and/or different diameters. For example, two arms of the first stent graft module can have the same diameter, for example ca. 8 mm in each case, and one arm can have a diameter of ca. 14 mm. As is customary in the field in question, "ca." means that the scope of the invention also includes measurement and production tolerances just above or below the aforementioned numerical values and the ones indicated hereinbelow, for example 8.4 or 14.3.

According to another embodiment, two arms of the second stent graft module have a diameter of ca. 8 mm, and one arm has a diameter of ca. 16 mm. In this example, the arm with the diameter of ca. 16 mm is longer than the two other arms and is interlocked (i.e. guided or moved) into the above-described arm of the first stent graft module with the diameter of ca. 14 mm. By virtue of the slightly larger diameter of the arm of the second stent graft module, the radial pressure results in a firm anchoring of the second stent graft module in the first stent graft module.

It will be appreciated that the bodies of the stent graft modules can also have different diameters and lengths. For example, the diameter of the body of the first stent graft module can have a diameter of between ca. 24 and ca. 36 mm, preferably of ca. 32 mm. The length of the body of the first stent graft module can be ca. 83 mm, measured from the proximal end of the body, still covered by graft material, to the distal end of the longest arm.

In an embodiment, the body of the second stent graft module can also have different lengths and diameters. For example, the diameter of the second stent graft module is between ca. 20 and 32 mm, and preferably 28 mm.

According to another embodiment, the first stent graft module accordingly has one arm longer than and with a larger diameter than the two other arms. In a development of this embodiment, the two other arms of the first stent graft module thus have a smaller but identical diameter, but they differ from each other in length.

According to a further embodiment, two arms of the second stent graft module have the same length. In a development, it is therefore preferable if the second stent graft module has one arm longer than and with a larger cross section than the at least two other arms.

In a further embodiment of the aforementioned embodiment, the first stent graft module and the second stent graft module are connectable to each other by means of the respective longer arms of the stent graft modules being interlocked or guided into each other.

In another further embodiment, the first stent graft module has, at its proximal end, a stent that is largely free of graft material.

This embodiment has the advantage that a secure anchoring in the vessel can be obtained by the area free of graft material. In the course of their self-expansion, the arches or supports of the stent firmly position themselves on the vessel wall, and it is therefore preferable in this case if the first stent graft module is positioned first of all, and the second stent graft module is connected to the first one via the arms being guided or interlocked into each other.

Here, "largely free of graft material" means that most of the stent is not covered by graft material, and it is only for the purpose of connection to the other stents of the stent graft that it is connected to these by the graft material. It may therefore be sufficient if only the outermost tips of the distally pointing arches of the outermost stent is covered with graft material.

It will be appreciated that the stent free of prosthesis material/graft material at the proximal end of the first stent graft module and the arches or supports of this stent can have a variable length, and this length can be suitably adapted depending on the location and nature of the vessel.

In another embodiment, two arms of the second stent graft module are formed at an angle to the tubular longitudinal direction of the stent graft. The angle to the longitudinal direction of the body of the stent graft module can be from ca. 0 to ca. 45°, in particular ca. 30°. This embodiment has the advantage that an optimal connection to the anatomically branching-off vessels, for example the renal arteries, can be established.

In yet another embodiment of the stent graft according to the invention, with respect to the diameter of the second body, the longer arm of the second stent graft module is arranged centrally and the at least two other arms are arranged at the edges.

The present invention further relates to a stent graft kit having at least two modular stent grafts according to the invention, i.e. at least four stent graft modules. This kit affords the advantage of being flexible and of being able to be assembled in accordance with the particular patient or with the vessel anatomy of the latter. It is obviously preferable in this case if the two modular stent grafts have different body lengths and body diameters, in order to permit still more flexible use. This kit is particularly advantageous in emergency situations and emergency operations where speed is of the essence and where there is no time for specific adaptation/configuration of a tailor-made stent graft.

Moreover, the present invention also relates to a method by which an above-described modular stent graft according to the invention is inserted into a blood vessel of a patient, or a method for treating a patient requiring insertion or placement of a stent graft, with the following successive steps:
  introducing the first stent graft module into the blood vessel to be treated,
  releasing the first stent graft module for expansion at a location to be treated in the blood vessel,
  introducing the second stent graft module into the same blood vessel to be treated, and
  partially inserting an arm of the second stent graft module into an arm of the first stent graft module and releasing the second stent graft module for expansion and for partial overlapping of the distal end of the arm of the first stent graft module with the proximal end of the arm of the second stent graft module.

The stent graft modules can be inserted and released using insertion and release systems known in the prior art. For example, reference is made here to the systems described in DE 10 346 200, DE 10 2006 004 123 and DE 10 2007 010 305, the content of which is hereby explicitly incorporated.

Alternatively, the stent graft modules can also be inserted in the reverse sequence, in which case the method then comprises the following steps:
  introducing the second stent graft module into the blood vessel to be treated,
  releasing the second stent graft module for expansion at a location to be treated in the blood vessel,
  introducing the first stent graft module into the same blood vessel to be treated, and partially inserting an arm of the first stent graft module into an arm of the second stent graft module and releasing the first stent graft module for expansion and for partial overlapping of the distal end of the arm of the second stent graft module with the proximal end of the arm of the first stent graft module.

In embodiments of the method according to the invention, the above-described advantageous developments of the modular stent graft according to the invention are used, for example with the respectively longest arms of the two stent graft modules being inserted into each other.

The invention further relates to the use of a modular stent graft according to the invention for the treatment of a blood vessel, wherein both modules of the modular stent graft are inserted into the same blood vessel.

Further advantages will become clear from the description and from the attached figures.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Illustrative embodiments of the invention are shown in the drawings and are explained in more detail in the description below.

FIG. 1 shows a schematic representation of an illustrative embodiment of a first stent graft module of the stent graft according to the invention, in a side view with graft material (1A), and schematically from the front without graft material (1B);

FIG. 2 shows a schematic representation of an illustrative embodiment of a second stent graft module of the stent graft according to the invention, in a side view with graft material (2A), and schematically from the front without graft material (2B);

FIG. 3 shows a schematic representation of another illustrative embodiment of a second stent graft module of the stent graft according to the invention, in a side view with graft material (3A), and schematically from the front without graft material (3B)

DESCRIPTION OF PREFERRED EMBODIMENTS

Figure 1A:
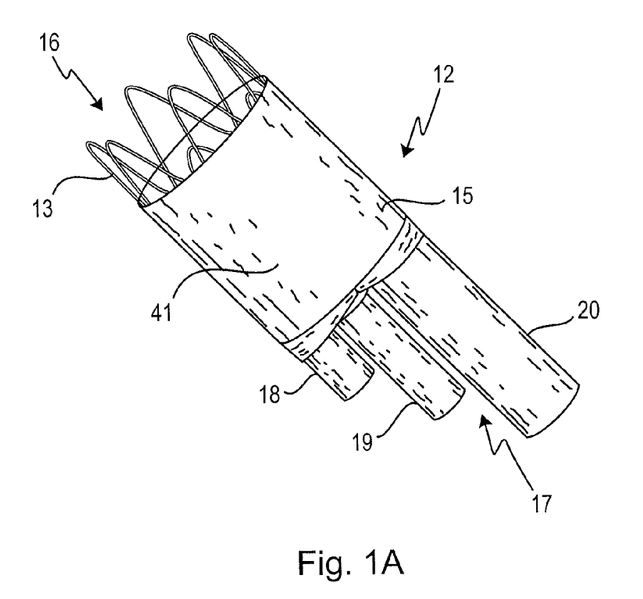
Figure 1B:
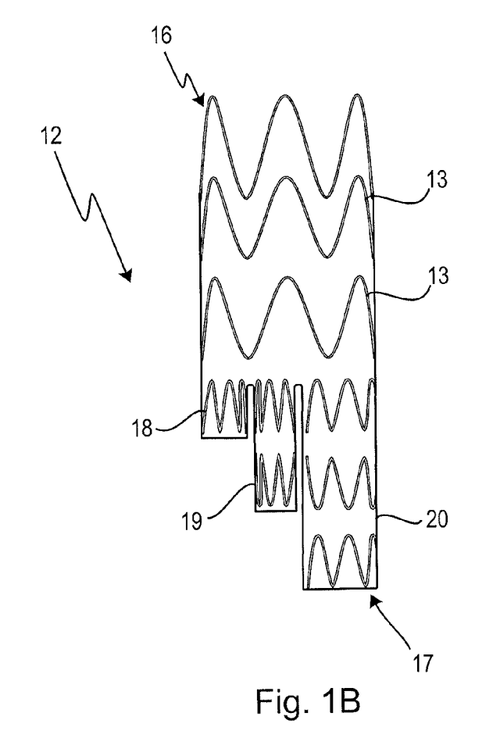
Figure 2A:
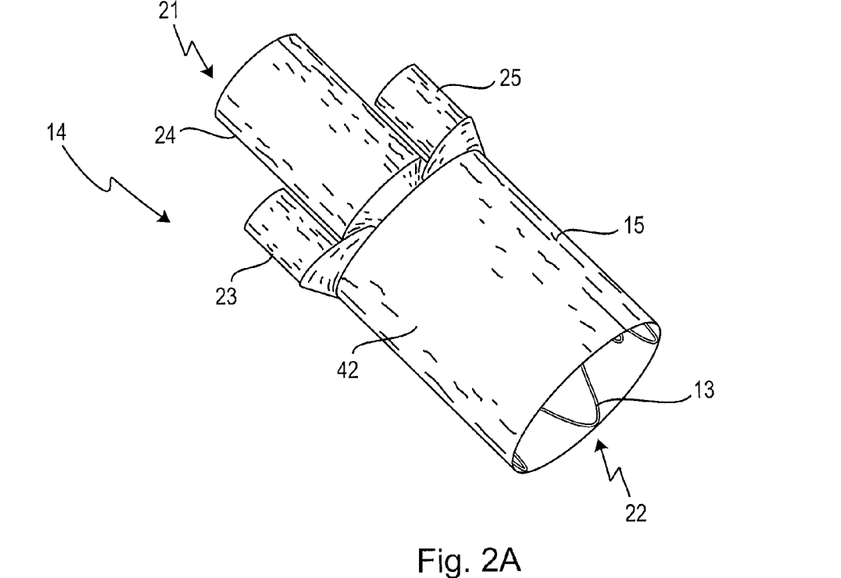
Figure 2B:
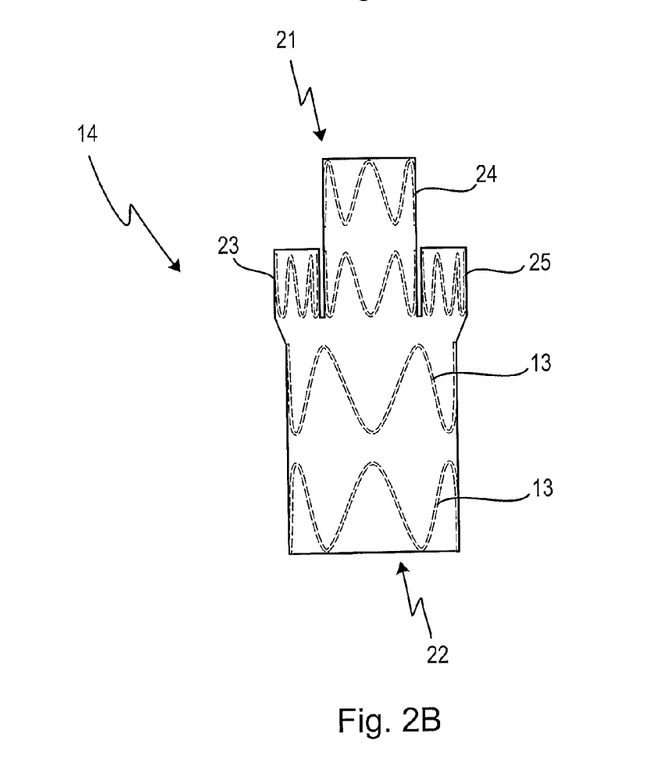

A first stent graft module is designated by 12 in FIGS. 1A and 1B, and a second stent graft module is designated by 14 in FIGS. 2A and 2B. Both stent graft modules 12, 14 have in each case a plurality of stents 13, which have meandering supports with arches alternately pointing in the proximal and distal directions. The stents 13 are also designated as "stent rings". The stents 13 of the stent graft modules 12, 14, preferably made from a self-expanding material with a shape-memory property, preferably Nitinol, are in each case connected by a biocompatible graft material 15; the latter is shown as transparent in FIGS. 1B, 2B and 3B only for explanatory purposes. The stent graft modules 12, 14 preferably have the same material 15, which consists of materials customarily used for stent grafts. Proceeding from the teaching disclosed herein, it will be clear to a person skilled in the art which materials can be used to obtain the stent graft according to the invention.

The stent graft module shown in FIGS. 1A and 1B, which has a body 41, a proximal end 16 and a distal end 17, also has, at the distal end 17, three arms 18, 19, 20 extending in the distal direction. The arm 20 has a larger diameter than the two other arms 18 and 19 and is also longer than these.

The stent graft module 14 shown in FIGS. 2A and 2B, which has a body 42, a proximal end 21 and a distal end 22, also has, at the proximal end 21, three arms 23, 24 and 25. In the embodiment of the stent graft module 14 shown in FIG. 2, the arm 23 is longer than the two other arms 24 and 25 and also has a larger diameter.

Figure 3A:
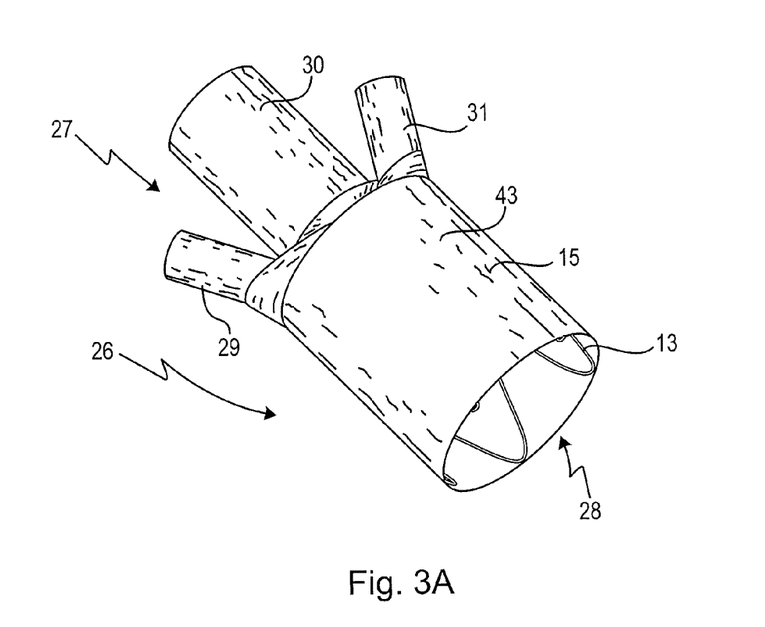
Figure 3B:
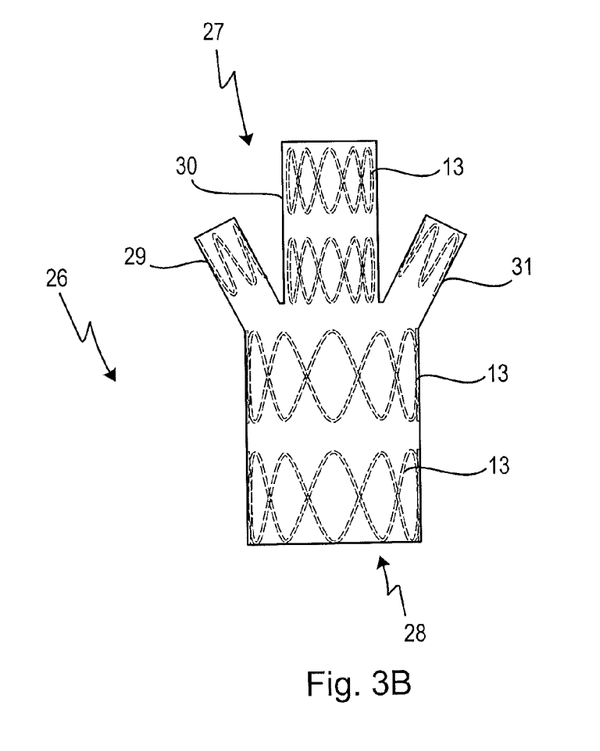

FIG. 3 shows an alternative further embodiment of the second stent graft module 26, with a body 43, a proximal end 27 and a distal end 28. This stent graft module 26 also has three arms 29, 30 and 31, the longer arm 30 here also having a larger diameter than the two other arms 29 and 31.

In the embodiment shown in FIG. 3, the arm 30 extends parallel to the longitudinal direction of the body 43, whereas the two arms 29 and 31 jut out at an angle from the longitudinal direction. The angle at which the two arms 29 and 31 jut out can be between 0° and ca. 30°.

Figure 4:
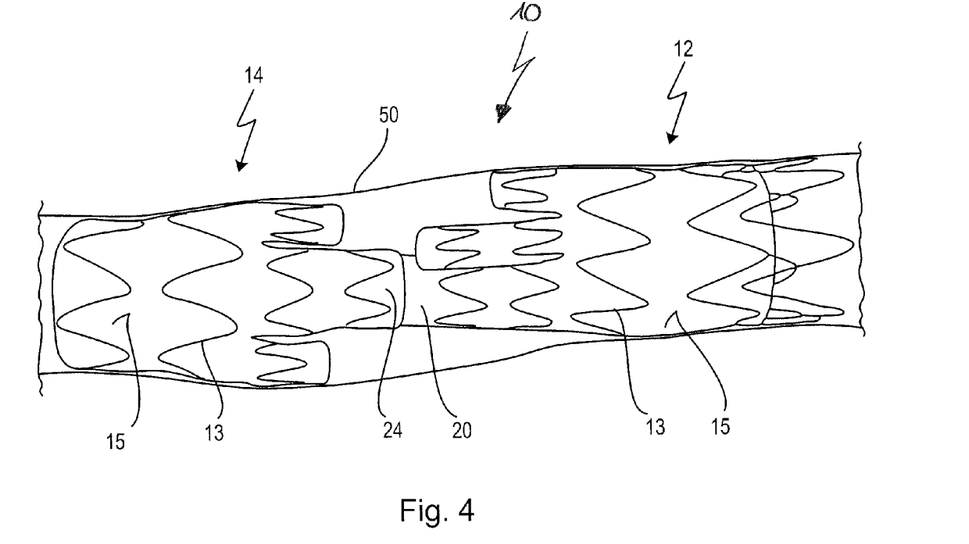
FIG. 4 shows in a side view, and with graft material, a schematic representation of an embodiment of the modular stent graft assembled from the first and second stent graft modules shown in FIGS. 1 and 2.

FIG. 4 shows an embodiment of the modular stent graft 10 according to the invention, assembled from the two stent graft modules 12 and 14. In the view shown in FIG. 4, the arm 20 of the first stent graft module 12 is partially inserted into the arm 24 of the second stent graft module 14 in such a way that the proximal end of the arm 24 overlaps the distal end of the arm 20. Therefore, in this embodiment, the diameter of the arm 20 is preferably larger than the diameter of the arm 24.

It will be appreciated that, as an alternative, the arm 24 of the second stent graft module 14 can also be inserted with a partial overlap into the arm 20 of the first stent graft module 12. In this case, the diameter of the arm 24 is preferably larger than the diameter of the arm 20 of the first stent graft module in order to ensure, after the expansion of the module and of the arm, a firm pressure and a resulting anchoring of the arm 24 in the arm 20.

In the view shown in FIG. 4, the modular stent graft 10 is inserted in a blood vessel 50. It will also be seen from this that the stent graft 10 is not assembled in a modular fashion at a bifurcation or on account of a bifurcation, and instead the modules 12 and 14 are situated within the same vessel 50 and are not present in branching-off blood vessels.

The invention claimed is:

1. A modular stent graft which is designed for introduction into a blood vessel of a patient in need thereof and which has stents connected by means of a graft material, wherein the stent graft has a first stent graft module with a body, a proximal end, and a distal end, and with at least two tubular arms which extend longitudinally in the distal direction from the distal end of the first stent graft module and which are integrally connected to the body of the first stent graft module, wherein the first stent graft module has one arm longer than and with a larger diameter than the at least second other arm, a second stent graft module with a second body, a proximal end, and a distal end, and with at least three tubular arms which extend longitudinally in the proximal direction from the proximal end of the second stent graft module and which are integrally formed with the body of the second stent graft module, wherein the second stent graft module has one arm longer than and with a larger cross section than the at least two other arms, wherein arms of the first stent graft module and of the second stent graft module in each case have diameters such that the first and second stent graft modules are connectable to each other by interlocking one into the other and by partially overlapping the respective one arm of the distal end of the first stent graft module with the arm of the proximal end of the second stent graft module in order to form an assembled modular stent graft within the same blood vessel, wherein the first stent graft module and the second stent graft module are connectable to each other by means of the respective longer arms of the stent graft modules being interlocked into each other.

2. The stent graft as claimed in claim 1, wherein the first stent graft module and the second stent graft module are connectable by interlocking an arm of the second stent graft module into an arm of the first stent graft module and by having them partially overlap.

3. The stent graft as claimed in claim 1, wherein the first stent graft module and the second stent graft module are connectable by interlocking an arm of the first stent graft module into an arm of the second stent graft module and by having them partially overlap.

4. The stent graft as claimed in claim 1, wherein the first stent graft module has between two and four arms, in particular three arms.

5. The stent graft as claimed in claim 1, wherein the arms of the first stent graft module and/or of the second stent graft module have different lengths and/or different diameters.

6. The stent graft as claimed in claim 1, wherein at least two arms of the second stent graft module have the same length.

7. The stent graft as claimed in claim 1, wherein the first stent graft module has, at its proximal end, a stent that is largely free of graft material.

8. The stent graft as claimed in claim 1, wherein at least two arms of the second stent graft module are formed at an angle to the tubular longitudinal direction of the second stent graft module.

9. The stent graft as claimed in claim 1, wherein, with respect to the diameter of the second body, the longer arm of the second stent graft module is arranged centrally and the at least two other arms are arranged at the edges.

10. A stent graft kit comprising at least two modular stent grafts as claimed in claim 1.

\* \* \* \* \*